(12) United States Patent
Sharma et al.

(10) Patent No.: US 8,704,016 B2
(45) Date of Patent: Apr. 22, 2014

(54) SMB PROCESS FOR THE PURIFICATION OF ETHANOL AND BUTANEDIOL WITH INTEGRATED REGENERATION

(71) Applicant: OROCHEM Technologies, Inc., Lombard, IL (US)

(72) Inventors: Deepak Sharma, Naperville, IL (US); Rahul K. Keswani, Lisle, IL (US); Wahab Mahmood, Niles, IL (US); Asha A. Oroskar, Oak Brook, IL (US)

(73) Assignee: OROCHEM Technologies, Inc., Naperville, IL (US)

( * ) Notice: Subject to any disclaimer, the term of this patent is extended or adjusted under 35 U.S.C. 154(b) by 0 days.

(21) Appl. No.: 13/837,355

(22) Filed: Mar. 15, 2013

(65) Prior Publication Data

US 2013/0317261 A1    Nov. 28, 2013

Related U.S. Application Data

(63) Continuation-in-part of application No. 13/478,160, filed on May 23, 2012.

(51) Int. Cl.
*C07C 29/76* (2006.01)

(52) U.S. Cl.
USPC ........... 568/913; 568/917; 435/161; 435/132; 435/140

(58) Field of Classification Search
USPC .................. 568/913, 917; 435/161, 132, 140
See application file for complete search history.

(56) References Cited

U.S. PATENT DOCUMENTS

| | | | |
|---|---|---|---|
| 2,985,589 A | 5/1961 | Broughton | |
| 4,321,328 A | 3/1982 | Hoge | |
| 4,333,740 A | 6/1982 | Priegnitz | |
| 5,156,736 A | 10/1992 | Schoenrock | |
| 5,755,967 A | 5/1998 | Meagher | |
| 6,476,239 B1 | 11/2002 | Arumugam | |
| 6,872,314 B2 | 3/2005 | Boyd | |
| 6,896,811 B2 | 5/2005 | Heikkila | |
| 7,166,460 B2 | 1/2007 | Wilkins | |
| 7,229,558 B2 | 6/2007 | Heikkila | |
| 7,399,898 B2 | 7/2008 | Lee | |
| 7,507,273 B1 | 3/2009 | Massie | |
| 8,119,378 B2 | 2/2012 | Simpson | |
| 2006/0251762 A1 | 11/2006 | Jansen | |
| 2010/0099155 A1 | 4/2010 | Frank | |
| 2010/0323417 A1 | 12/2010 | Simpson | |
| 2011/0160483 A1 | 6/2011 | Rezkallah | |

FOREIGN PATENT DOCUMENTS

WO    2008046635 A1    4/2008

OTHER PUBLICATIONS

Ken-Jer Wu, Saratale, GD., Lo, Y., Chen, W., Tseng, Z., Chang, M. Tsai, B., Su, A., Chang, J., "Simultaneous Production OD 2,3-Butanediol, Ethanol and Hydrogen With *Klebsiella* sp. Strain Isolated From Sewage Sludge", Bioresource Technology, 2008, vol. 99, pp. 7966-7970, Elsevier.

A.N. Anozie, Okuhon, EE, Osoulale, FN, Adewole, JK, Dehydration of Ethanol-Water Mixture Using Activated Carbons From Sawdust and Palm Kernel Shells, Separation Science and Technology, vol. 45, pp. 1482-1489, Published Online Jun. 15, 2010, Taylor & Francis, England.

ISR and WO related to PCT/US2013/041850 (Corresponding to U.S. Parent Case U.S. Appl. No. 13/478,160), mailed Sep. 23, 2013 by KIPO.

*Primary Examiner* — Elvis O Price
(74) *Attorney, Agent, or Firm* — Richard P. Silverman & Assoc., LLP

(57) ABSTRACT

Disclosed is an improved SMB process incorporating novel regeneration steps for the separation of ethanol associated oxygenates such as butanediol from a dilute mixture of ethanol and associated oxygenates in water in the presence of organic compounds derived from a biofermentation process. Applicant discovered that increasing the number of raffinate streams alone or in combination with a hot regeneration zone within the SMB cycle can significantly reduce the capital and operating costs associated with the incorporation of the SMB process in a complex for the production of ethanol and butanediol from biofermentation effluent. The process is useful for removing water from dilute aqueous mixtures of organic compounds comprising ethanol in dilute concentration in water and produced by fermentation, biomass extraction, biocatalytic and enzymatic processes which are not economically recoverable by conventional distillation methods.

16 Claims, 9 Drawing Sheets

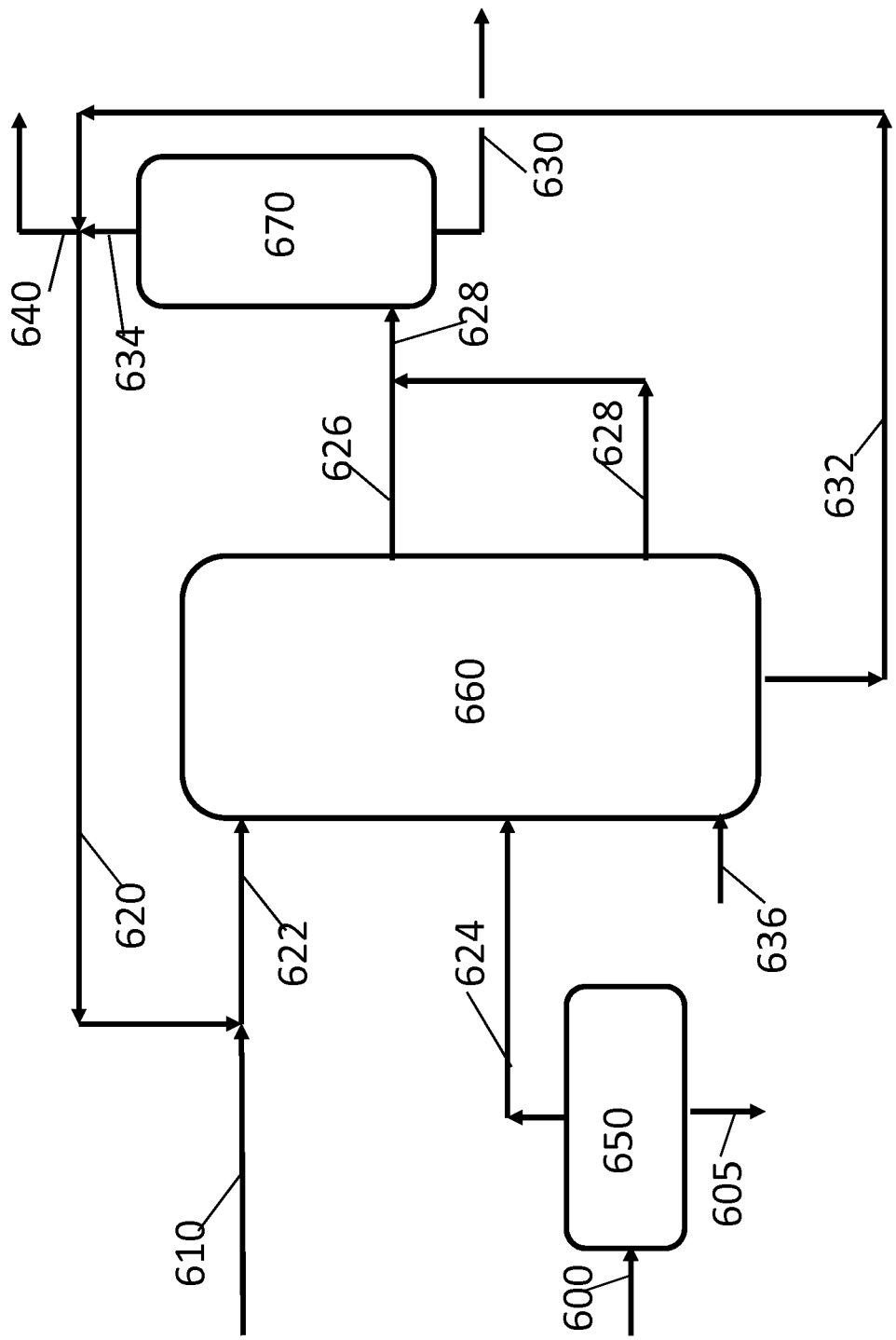

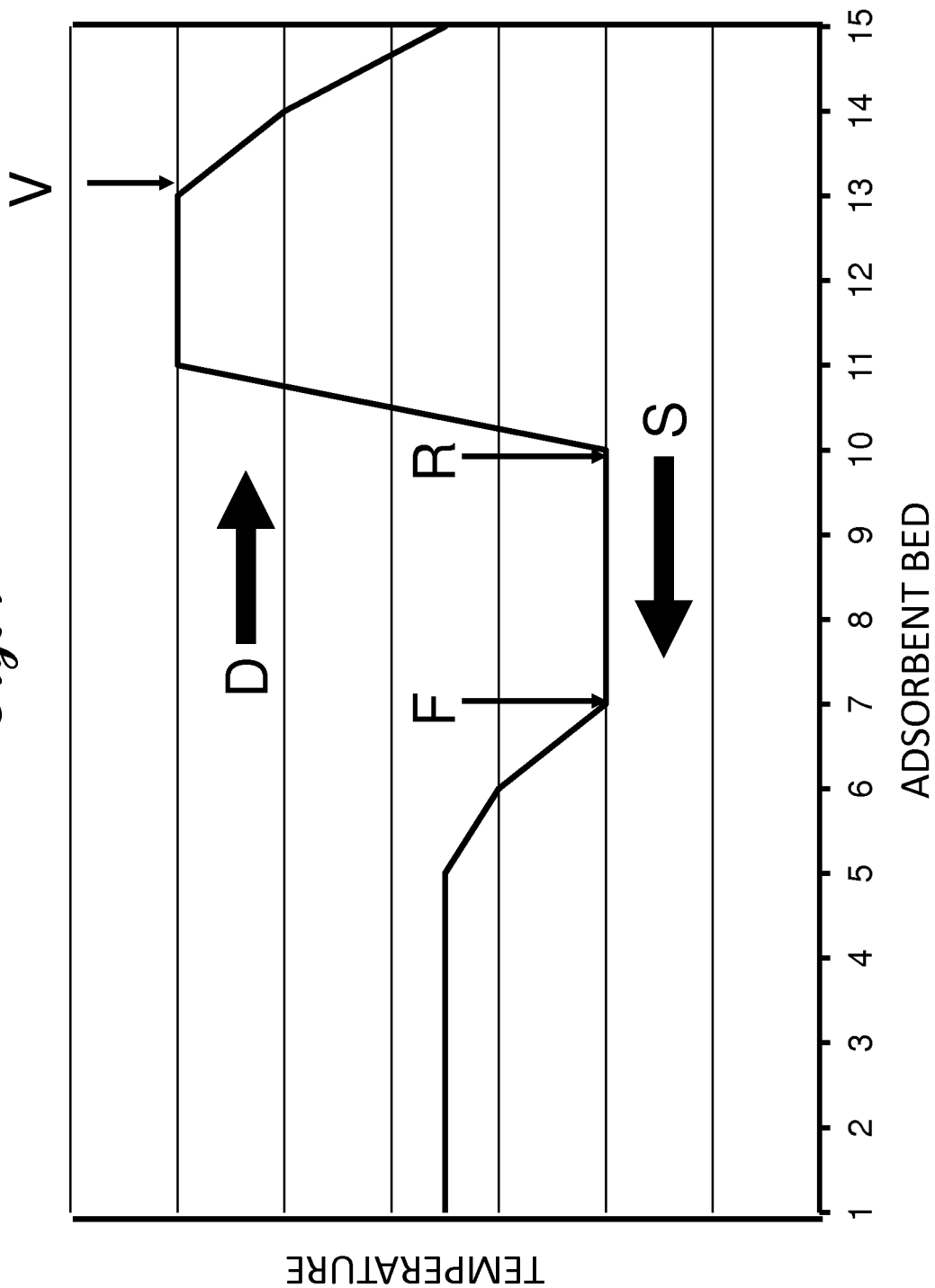

SMB PROCESS FOR THE PURIFICATION OF ETHANOL AND BUTANEDIOL WITH INTEGRATED REGENERATION

CROSS-REFERENCE TO RELATED APPLICATIONS

The present application is a continuation-in-part of U.S. patent application Ser. No. 13/478,160, filed May 23, 2012, which is hereby incorporated by reference.

FIELD OF THE INVENTION

The present invention relates to an improved simulated moving bed process for the recovery of ethanol and butanediol from a fermentation extract. More particularly, the presentation relates to a simulated moving bed process which incorporates an integrated liquid and vapor regeneration steps in the SMB cycle to provide additional raffinate streams. Most particularly, the integrated vapor regeneration sequence employs streams such as steam, heated azeotropic ethanol, and superheated ethanol vapor to significantly reduce the capital and reduce the operating cost of the SMB complex and reduce the possibility of contaminating the fermentor.

BACKGROUND OF THE INVENTION

The separation of organic compounds from water has been an ongoing challenge for the chemical industry. Typically, techniques such as distillation, decantation, extraction, evaporation, and chromatography have been employed. These methods, however, often are energy intensive, expensive to operate, and may not be practical or economical for the recovery and purification of materials from dilute aqueous solutions. For example, chemical products such as glucose, which is isolated from biomass, and fermentation products such as lactic acid, phenylalanine, citric acid, L-amino acids, succinic acid, and ascorbic acid, typically must be separated, recovered, and purified from dilute aqueous solutions or fermentation broths. The recovery costs for such fermentation processes are often the major factor which determines their commercial success. The presence of water in chemical products also often complicates purification methods such as crystallization, waste disposal methods, such as incineration, and the recovery and recycling of solvents.

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow. There are hundreds of adsorbents which have been used for simulated moving bed systems, some of which include resins, zeolites, alumina, and silica.

Simulated Moving Bed (SMB) technology represents a variation on the principles of high performance liquid chromatography. SMB can be used to separate particles and/or chemical compounds that would be difficult or impossible to separate by any other means. Furthermore, SMB technology represents a continuous process which provides a significant economic and efficiency advantages in manufacturing operations compared to batch typical batch separation methods including crystallization and stepwise chromatographic separations.

The continuous nature of SMB operation is characterized by very brief flow stoppages during the port switchovers in successive process steps. However, since all input and output conduits briefly stop at the same time, there are no significant pressure drops or surges in the system. Indexing of mechanical rotors is designed to effect rapid switchovers, even on very large industrial machines. Further, strategy in the design of process configuration is largely dictated by the affinity and release characteristics of bound species to the solid substrate, exclusion properties of unbound species, the bed volume required to obtain separation of by-product, and other factors.

There are more than 200 issued patents on modifications of SMB technology that disclose improvements in separation efficiency generally, or in particular applications, enhanced purity and yield in the final products, or reduction in required volume desorbent. For example, in one variation disclosed in U.S. Pat. No. 5,156,736, separations are performed in a single bed preserving the principles of SMB by interposing at various levels in the bed a series of crossectionally functional collection and distribution means for adding feedstock and recycled process liquid, collecting raffinate, distributing eluent, and recovering extract product. Equilibrium is established in the system by very precise flow and pressure control.

U.S. Pat. No. 4,333,740 discloses an absorptive process for separating water from a feed mixture comprising ethanol and water, which comprises contacting the feed mixture with an adsorbent comprising corn meal, selectively adsorbing substantially all of the water to be separated to the substantial exclusion of the ethanol, and thereafter recovering high purity ethanol. The process employs a countercurrent moving bed or simulated moving bed countercurrent flow system.

In U.S. Pat. No. 5,755,967 discloses the use of a new composite membrane and a method for recovery of acetone and butanol using pervaporation. In the technique molecules are selectively adsorbed by a membrane and are caused to diffuse across the membrane through a driving force such as vacuum.

U.S. Pat. No. 7,166,460 discloses a bioprocess engineering solution for a product removal process for use in biofermentation. The invention discloses a process for withdrawing an aliquot of broth from a biofermentation vessel during at least a portion of the biofermentation, removing biocatalyst and water, chromatographically separating biofermentation products from the withdrawn broth using water as an eluent, and returning the remaining components of the broth back to the biofermentation vessel. The continuous chromatic separation process is disclosed to be counter-current chromatography or simulated counter-current chromatography, including simulated moving bed chromatography. However, the reference states that process chromatography methods are unable to selectively separate biofermentation products and recycle the other media components to the biofermentor. This occurs because a portion of the eluent required to drive chromatographic separation would accumulate in the biofermentor, reducing its capacity.

US Publication No. 2010/0099155 discloses apparatuses and processes for the removal and production of fermentation prepared one or more volatile organic compounds. The apparatuses comprise a fermentor unit, a vacuum side stripper unit, and optionally one or more pressure swing adsorption unit, a dual-function column, a dividing wall distillation column, and a means for inducing phase separation of a mixture of volatile compounds and water.

Biofermentation processes provide a fermentation product stream which comprises water, ethanol, non-condensable gases such as methane, nitrogen, carbon dioxide, and hydrogen, oxygenated organic compounds and soluble biomass materials. Oxygenated chemicals such as ethanol have been traditionally produced from sugar sources, such as corn, sugarcane, molasses, etc. Other associated oxygenates produced with ethanol by fermentation often include isopropanol, propanediols, butanediols, and acetic acid. For example, it is well known that 2,3-butanediol can be produced by fermentation techniques. Examples of some species of bacteria such as *Bacillus polymyxa* and *Klebsiella pneumoniae* have been disclosed to convert both glucose and xylose into mixtures of predominantly 2,3 butanediol and ethanol. Also, the production of 2,3-butanediol has been disclosed using arabinose as a feedstock. A summary of such methods entitled, "Bulk Chemicals from Biomass", by Jacco van Haveren, et al. was published online in Wiley InterScience. More recently, ethanol has been produced by the fermentation of gases such as carbon monoxide. The LANZATECH Process (Available from LanzaTech Inc., Parnell Auckland, New Zealand) uses microbial gas fermentation to convert any carbon monoxide containing gases produced by industries such as steel manufacturing, oil refining and chemical production, as well as gases generated by gasification of forestry and agricultural residues, municipal waste, and coal into valuable fuel and chemical products to produce ethanol and other molecules, such as 2,3-butanediol. A description of the LANZATECH microbial gas fermentation process is disclosed in U.S. Publication No. US20100323417 and in U.S. Pat. No. 8,119,378, which are hereby incorporated by reference.

Co-pending U.S. application Ser. No. 13/478,160, filed May 23, 2012, discloses an SMB process for recovering ethanol and 2,3 butanediol derived from fermentation effluent, wherein during the SMB cycle, at least one of the adsorption beds is regenerated with methanol, ethanol, propanol and the stationary phase agent is a fluorinated carbon adsorbent.

The known methods for dewatering organic compounds are limited primarily to organic acids and typically utilize a strong charge-charge interaction between the acid and adsorbent, such as ion-exclusion, as the primary separation mechanism. Because such charge-charge interactions are weak or non-existent for neutral organic compounds, these methods are not, in general, applicable for dewatering organic compounds without carboxyl substituents.

SUMMARY OF THE INVENTION

The recovery and purification of ethanol and butanediol from fermentation products is highly energy intensive because the ethanol and butanediol are in the presence of water. In a typical SMB system, it is an objective to operate the SMB adsorption, desorption and regeneration steps at a uniform temperature and pressure such that all of the streams remain in the liquid phase However, at these uniform conditions, the desorption of the key component from the stationary phase agent may require excessive amounts of desorbent, additional adsorbent beds, or additional external purification of the desorbent. Such amendments to the SMB process can result in significant increases in capital and operating costs. Applicant discovered that the use of ethanol as the desorbent combined with employing a superheated ethanol vapor to desorb the SMB adsorbent beds undergoing regeneration in the SMB cycle, or by using an azeotropic mixture of ethanol and water as the desorbent combined with using steam to desorb the adsorbent beds undergoing regeneration can significantly reduce capital cost and operating costs of the complex by elimination of an external distillation column to purify the desorbent. Furthermore, SMB systems typically have only a single raffinate stream for the recovery of the least adsorbent component in the feed. Applicant has surprisingly discovered that employing multiple raffinate streams alone, or in combination with enhanced regeneration techniques at elevated temperatures relative to the liquid separation zone provide significant process flexibility and reduced capital and operating costs.

In one embodiment, the present invention a multi-raffinate simulated moving bed (SMB) process for the separation of ethanol and butanediol from an aqueous biomass effluent stream from a fermentor. The biomass effluent stream comprises water, ethanol, butanediol, and suspended solids. The multi-raffinate SMB process has an SMB zone comprising a desorption zone, a rectification zone, an adsorption zone, and at least one regeneration zone. The process comprises passing the aqueous biomass effluent stream to a pretreatment zone including a naturation zone and a filtration zone to remove suspended solids and naturate any biomass solids to provide an SMB feed stream. The SMB feed stream at an effective feed temperature and a mobile phase desorbent stream at an effective desorbent temperature are passed to the SMB zone. The mobile phase desorbent stream comprises a $C_1$ to $C_3$ alcohol. The SMB zone comprises a plurality of n adsorbent beds each adsorbent bed having a top and a bottom, wherein the desorption zone, rectification zone, adsorption zone, and the at least one regeneration zone comprise one or more of the adsorbent beds. Each adsorbent bed contains a stationary phase adsorbent selected from the group consisting of a fluorinated carbon adsorbent and a modified C18 silica gel. Each of the adsorbent beds of the desorption zone, rectification zone, adsorption zone are disposed in a serial configuration wherein the bottom of each adsorbent bed i is in fluid communication with the top of the i+1 adsorbent bed, to provide an extract stream comprising ethanol and butanediol withdrawn from the desorption zone, and a primary raffinate stream withdrawn from the adsorption zone. At least a portion of the primary raffinate stream is passed to the at least one regeneration zone to provide at least one secondary raffinate stream. The extract stream is passed to a product recovery zone to separate and recover ethanol and butanediol products from the extract stream.

BRIEF DESCRIPTION OF THE DRAWINGS

FIG. 8 is a schematic process flow diagram representing an embodiment of the present invention for a simulated moving bed adsorption process illustrating the separate recovery of ethanol product, and 2,3-butanediol without a separate external ethanol distillation column.

FIG. 9 illustrates the temperature profile for an SMB zone operating according to one embodiment of the present invention for a 15 adsorbent bed SMB system.

DETAILED DESCRIPTION OF THE INVENTION

Figure 1:
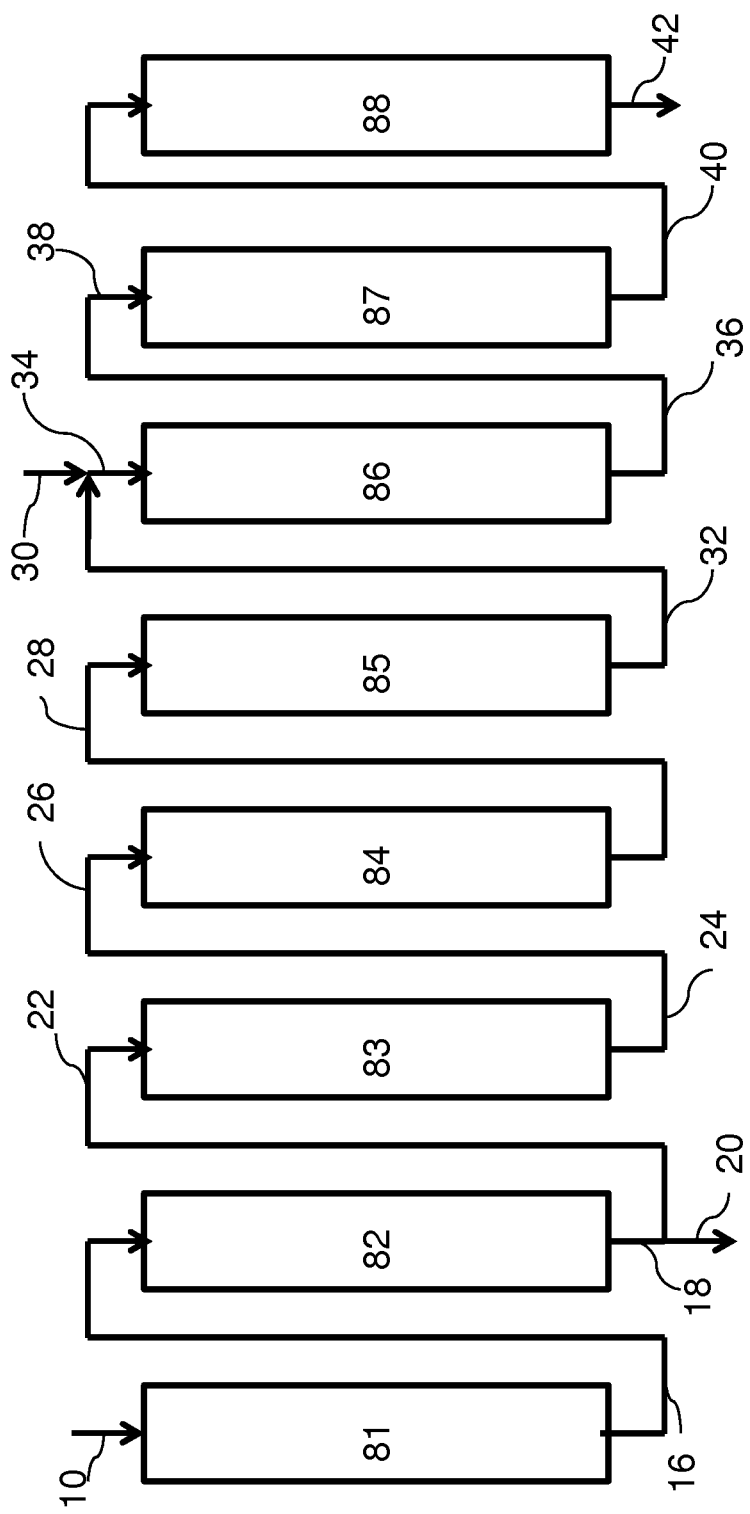
FIG. 1 is a schematic process flow diagram illustrating a liquid phase simulated moving bed separation zone for an 8 adsorbent bed arrangement for the purification of ethanol and butanediol.

The present invention relates to the separation and recovery of ethanol and butanediol produced in a fermentation process in a simulated moving bed (SMB) process with a selective stationary phase adsorbent and a suitable desorbent. One of the problems in commercializing a continuous SMB separation or purification process for the biomass feed stream, after the selection of the stationary phase agent and the mobile phase desorbent is finding an economically feasible method of recovering the mobile phase desorbent from the raffinate stream. This is especially a problem when the mobile phase desorbent is a water soluble oxygenate such as water, or an organic alcohol, and the feed stock is an aqueous solution. In such cases, the raffinate stream will comprise the least adsorbent species, the mobile phase desorbent, and a large amount of water. If the least adsorbent species or the mobile phase desorbent are able to from azeotropic mixtures, the recovery of the mobile phase desorbent can require a significant capital investment and operating costs. Methods are sought to reduce the reduce the mobile phase desorbent recovery capital and operating costs to significantly improve the economic viability of aqueous SMB separation and purification processes.

A traditional SMB separation process typically comprises passing a feed stream and a mobile phase stream to an SMB zone and recovering an extract stream and a raffinate stream. Applicant surprisingly discovered that by amending the traditional SMB process to include an expanded rectification zone to provide multiple raffinate streams, significant capital cost and operating cost savings could be obtained. Moreover, when the rectification zone comprised a heated vapor or superheated vapor regeneration step, some or all of the downstream mobile phase desorbent recovery costs can be eliminated.

DETAILED DESCRIPTION OF THE DRAWINGS

The SMB system of the current invention was arranged for maximum selectivity. The simulated moving bed operation is achieved by use of a plurality of adsorbent beds connected in series and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process. Feed enters and extract and raffinate streams are withdrawn continuously at substantially constant compositions. The overall operation is equivalent in performance to an operation wherein the fluid and solid are contacted in a continuous countercurrent manner, without the actual movement of the solid, or stationary phase adsorbent.

The operation of the SMB system is carried out at a constant temperature within the adsorbent bed. The feed stream is introduced and components are adsorbed and separated from each other within the adsorbent bed. A separate liquid, the mobile phase desorbent, is used to counter currently displace the feed components from the pores of the stationary phase adsorbent. During the SMB cycle of the present invention, adsorbent beds are advanced through a desorption zone, a rectification zone, an adsorption zone, and a regeneration zone. The description of the SMB cycle as a 2-3-3 cycle means that in the cycle, 2 adsorbent beds are in the rectification zone, 3 adsorbent beds are in the rectification zone, and 3 adsorbent beds are in the adsorption zone.

FIG. 1, as disclosed in co-pending application Ser. No. 13/478,160 shows an embodiment of a nominally isothermal all liquid phase simulated moving bed SMB adsorption zone based on an 8 adsorbent bed arrangement for the purification of ethanol and butanediol. Adsorbent beds 81-88, containing a stationary phase adsorbent selected from the group consisting of a fluorinated carbon adsorbent, and a modified C18 silica gel are disposed in a serial configuration such that in accordance with a prearranged cycle, conduit 16 provides fluid communication between the bottom of adsorbent bed 81 with the top of adsorbent bed 82, conduits 18 and 22 provide fluid communication between the bottom of adsorbent bed 82 bed and the top of adsorbent bed 83, conduit 26 provides fluid communication between the bottom of adsorbent bed 83 with the top of adsorbent bed 84, conduit 28 provides fluid communication between the bottom of adsorbent bed 84 with the top of adsorbent bed 85, conduits 32 and 34 provide fluid communication between the bottom of adsorbent bed 85 with the top of adsorbent bed 86, conduit 36 provides fluid communication between the bottom of adsorbent bed 86 with the top of adsorbent bed 87, conduit 40 provides fluid communication between the bottom of adsorbent bed 88 with the top of adsorbent bed 88, and conduit 42 provides for the withdrawal of fluid from the bottom of adsorbent bed 88. According to the prearranged SMB cycle, an SMB zone feed stream is passed to the isothermal SMB adsorption zone in line 30 and 34 to adsorbent bed 86. A raffinate stream is withdrawn from conduit 42, and an extract stream is withdrawn via conduits 18 and 20 from adsorbent bed 82. A liquid desorbent stream selected from the group consisting of methanol, ethanol, and methyl tertiary-butyl ether (MTBE) is introduced to adsorbent bed 81 in conduit 10. The adsorbent beds 81-88 are indexed according to a 2-3-3 SMB cycle such that at least 2 adsorbent beds undergo desorption, at least 3 adsorbent beds undergo rectification, and at least 3 adsorbent beds undergo adsorption during the SMB cycle. The objective is to recover ethanol and 2,3-butanediol with some methanol in the extract. The extract should contain less than 0.5% moisture.

The raffinate from the SMB zone should contain only water because the raffinate is returned to the fermentation broth. In the above eight column system, when the desorbent is methanol, it is difficult to remove methanol from the raffinate. To assure the essentially complete removal of methanol from the raffinate, the methanol must be removed from the adsorbent bed before the adsorbent bed is moved to the position in the predetermined cycle were the raffinate is pushed out through that adsorbent bed. This further removal of desorbent from the raffinate can be accomplished by the addition of an isolated regeneration step to purge any residual desorbent from the adsorbent bed prior to the introduction of the desorbent to the SMB system.

Although not shown in FIG. 1, an SMB feed stream which is derived from a process such as a biomass fermentor will require pretreatment before being introduced to the SMB zone. This pretreatment will vary depending upon the objective of the overall complex. For example, biomass effluent may contain acidic species, such as acetic acid. Complete neutralization of the biomass effluent will convert the acetic acid to less valuable components. Thus, as a general rule, pretreatment by neutralization of the biomass effluent will be carried out only to the degree necessary to protect the stationary phase adsorbent while retaining as much of the valuable acetic acid species as required.

Hot Vapor Regeneration in the SMB Cycle

Typically, an SMB unit is operated with a single valve or valve control system in an all liquid medium and generally all process temperatures and pressures do not vary or are maintained such that all streams remain liquid throughout the process. In the cases which will be discussed hereinbelow, such SMB operations with liquid regeneration methods for SMB regeneration steps are compared to the embodiments of the present invention for SMB operations wherein with the same single valve or valve control system, the regeneration is carried out with a combination of vapor and heated vapor regenerant streams in the same SMB cycle with the desorption, rectification and adsorption steps taking place in the liquid phase. In the present invention, a primary regeneration and secondary regeneration zone is established and integrated such that the secondary regeneration zone achieves a desired regeneration temperature. The feed temperature, that is the temperature at which the feed stream is introduced, and the temperature of the raffinate stream at raffinate temperature, are selected to return the heated adsorbent zones to a stable liquid phase temperature for the operation of the desorption, rectification and adsorption steps in the liquid phase. FIG. 9 illustrates the temperature profile for an SMB zone operating according to one embodiment of the present invention for a 15 adsorbent bed SMB system. In a given cycle, adsorbent beds, in position 1-10 are operating in a liquid phase wherein beds 1-3 are in the desorption zone, beds 4-6 are in the rectification zone, and beds 7-10 are in the adsorption zone. Thus, in the SMB cycle, while the mobile phase desorbent flows from low number adsorbent bed to high number adsorbent bed, the temperature profile over the liquid phase is decreasing; simultaneously, the simulated movement of the adsorbent beds from high number bed to low number bed requires the cooling of the adsorbent beds as they enter the liquid phase operation zones. The regeneration zones comprise a primary regeneration zone (bed 11) and a secondary regeneration zone. (beds 12-15). According to one embodiment of the invention, superheated ethanol at a temperature of about 110 to about 130° C. is simultaneously introduced at the top of the adsorbent beds in the secondary regeneration zone. This serves to raise and maintain the regeneration temperature in the secondary regeneration zone to a desired regeneration temperature. This is shown in FIG. 8 by the increase in temperature from the last bed (15) toward the first adsorbent bed in the secondary regeneration zone. The effluent from each of the adsorbent beds in the secondary regeneration zone is collected and a portion is returned to the top of the beds in the secondary regeneration zone to provide the superheated ethanol regeneration stream. A portion of the effluent from the secondary regeneration zone is passed to a condenser to provide a condensed ethanol stream. The primary regeneration zone uses an inert gas such as nitrogen or carbon dioxide to purge the adsorbent bed(s) in the primary adsorbent zone to recover any additional superheated or vaporized regenerant, such as ethanol, which is passed to the condenser and combined with the condensed ethanol stream. By way of example in the superheated ethanol scheme illustrated in FIG. 5 hereinbelow, the transition from the vapor phase operation of the primary and secondary regeneration is accomplished with cooling provided by the introduction of a cool feed stream at the top of adsorbent bed 5, and the introduction of a cool raffinate stream in adsorbent bed 10. Preferably, the feed temperature ranges from about 20 to about 50° C., and preferably the temperature at which the cool raffinate is introduced to the last bed in the liquid phase adsorption zone is between about 20 to about 50° C. The effective desorbent temperature ranges from about 50° C. to about 80° C. As described hereinbelow in FIG. 4, the regeneration vapor in the secondary regeneration zone is provided by steam, and the purge gas comprises carbon dioxide.

Figure 2:
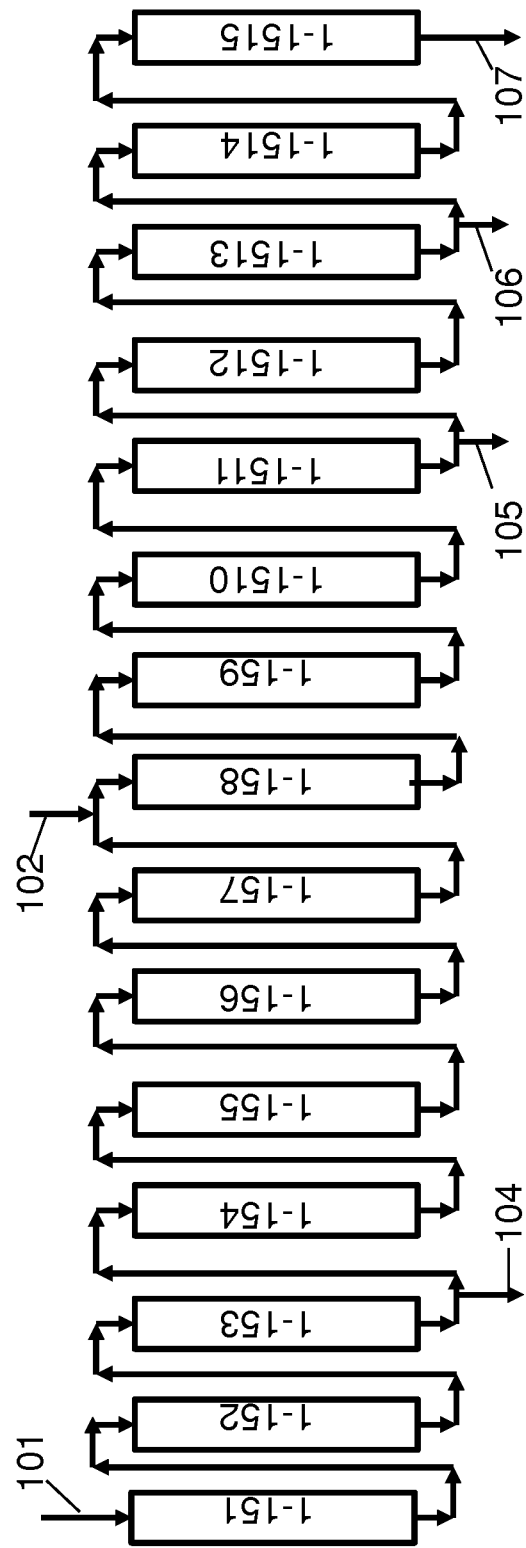
FIG. 2 is a schematic process flow diagram representing one embodiment of the present invention for a 15 adsorbent bed simulated moving bed adsorption process employing methanol as a desorbent for the dewatering of a fermentation effluent comprising ethanol and butanediol.

Referring to FIG. 2, which represents an all liquid phase embodiment of the present invention, an SMB using a methanol desorbent scheme for the separation of ethanol and butanediol from a fermentation effluent which produces an extract and 3 raffinate streams (a primary raffinate and two secondary raffinate streams). Referring to FIG. 2, a 15 adsorbent bed SMB arrangement is shown, wherein there are 15 adsorbent beds numbered 1-151 to 1-1515 which contain a stationary phase agent as described hereinabove. The 15 adsorbent beds operate in the liquid phase and represent a desorption zone (1-151 to 1-153), a rectification zone (1-154 to 1-157), an adsorption zone (1-158 to 1-1511), and a regeneration zone (1-1512 to 1-1515). Two raffinate stream, a primary raffinate in line 106, and a secondary raffinate stream in line 107. Each of the n=15 adsorbent beds has a top and a bottom and a plurality of flow lines are aligned to conduct the flow of fluid from the bottom of the first adsorbent bed 1-151 in a serial manner from the bottom of adsorbent bed i, where i ranges from 1 to n, to the top of adsorbent bed i+1 in the manner described hereinabove in FIG. 1. In FIG. 2, in each increment of the SMB cycle, a feed stream is introduced in the top of adsorbent bed 1-158 in line 102; the mobile phase desorbent is introduced in line 101 to the top of adsorbent bed 1-151; an extract stream is withdrawn in line 104 from the bottom of adsorbent bed 1-153; a primary raffinate stream is withdrawn in line 105 from the bottom of adsorbent bed 1-1511; a first secondary raffinate stream is withdrawn in line 106 from the bottom of adsorbent bed 1-1514; and, a second secondary raffinate stream is withdrawn in line 107 from adsorbent bed 1-1515. When the mobile phase is pure methanol, the extract stream in line 104 comprises ethanol, butanediol, and methanol, the primary raffinate comprises pure water, the first secondary raffinate comprises methanol and water, and the second secondary raffinate stream comprises pure methanol. The second secondary raffinate in line 107 can be recycled to provide at least a portion of the mobile phase desorbent in line 101. The extract is passed to downstream processing to recover the ethanol and butanediol.

Figure 3:
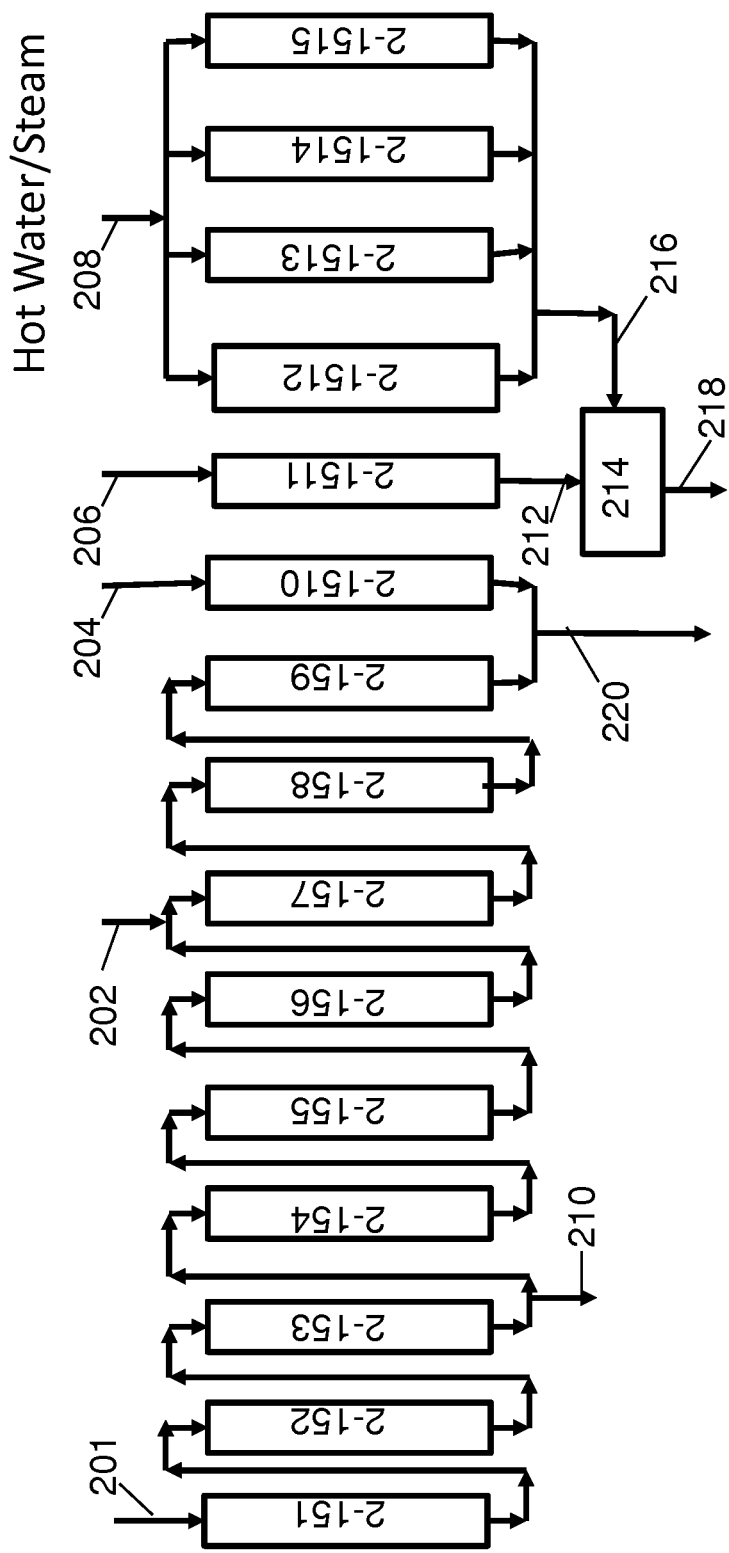
FIG. 3 is a schematic process flow diagram representing an embodiment of the present invention for a 15 adsorbent bed simulated moving bed adsorption process employing hot water or steam as a desorbent for the dewatering of a fermentation effluent comprising ethanol and butanediol.

Referring to FIG. 3, which represents a hot water or steam regeneration SMB using an ethanol desorbent scheme for the separation of ethanol and butanediol from a fermentation effluent, a 15 adsorbent bed SMB arrangement is shown, wherein there are 15 (n=15) adsorbent beds numbered 2-151 to 2-1515 which contain a stationary phase agent as described hereinabove. The first 10 beds of the 15 adsorbent beds operate in the liquid phase and represent a desorption zone (2-151 to 2-153), a rectification zone (2-154 to 2-156), and an adsorption zone (2-157 to 2-1510). The last five adsorbent beds comprise a primary regeneration zone (2-1511) and a secondary regeneration zone (2-1512 to 2-1515). Each of the first 9 adsorbent beds operating in the liquid phase (2-151 to 2-159) has a top and a bottom and a plurality of flow lines are aligned to conduct the flow of fluid from the bottom of the first adsorbent bed 2-151 in a serial manner from the bottom of adsorbent bed i to the top of adsorbent bed i+1. In each increment of the SMB cycle a feed stream is introduced in the top of adsorbent bed 2-157 via line 202, the mobile phase desorbent stream comprising pure ethanol is introduced to adsorbent bed 2-151 via line 201, an extract stream is withdrawn from adsorbent bed 2-153 in line 210, and a raffinate stream is withdrawn from adsorbent beds 2-159 and 2-1510 via line 220 as the primary raffinate stream. In the SMB cycle of the present invention as shown in FIG. 3, the adsorbent beds 2-151 to 2-159 are operating in a liquid state. The adsorbent beds 2-1510 to 2-1515 comprise a liquid regeneration zone, a purge zone, and a hot regeneration zone. Accordingly, a temperature profile is established in these regeneration zones, wherein the adsorbent beds undergoing the hot regeneration steps from 2-1515 are heated to the hot regeneration temperature, the purge zone and the liquid regeneration zone, and the introduction of the feed stream serve to return the adsorbent beds to the desired liquid SMB condition. A portion of the primary raffinate stream in line 220 is chilled in a chiller (not shown) to a chilled raffinate temperature of from about 20° C. to about 50° C. to provide a chilled raffinate stream which is passed to the top of adsorbent bed 2-1510 and introduced via line 204 to purge and to at least partially cool adsorbent bed 2-1510 (a liquid regeneration zone). A nitrogen stream in line 206 is passed to the top of adsorbent bed 2-1511 (a purge zone) to purge ethanol from adsorbent bed 2-1511 to provide a hot ethanol stream or purge zone effluent stream in line 212. Adsorbent beds 2-1512 to 2-1515 arranged in parallel as a hot regeneration zone and are purged with a hot water stream or a steam stream which is introduced at the top of the adsorbent beds 2-1512 to 2-1515 via manifold 208 and the hot regeneration effluent stream is collected in manifold 216 and together with the contents of line 212 is passed to a condenser 214 to condense the hot regeneration effluent stream comprising ethanol and provide a condensed regeneration effluent I stream or first secondary raffinate stream in line 218. At least a portion of the condensed ethanol stream following distillation (not shown) can be returned to the SMB to provide a portion of the mobile phase desorbent stream in line 201.

Figure 4:
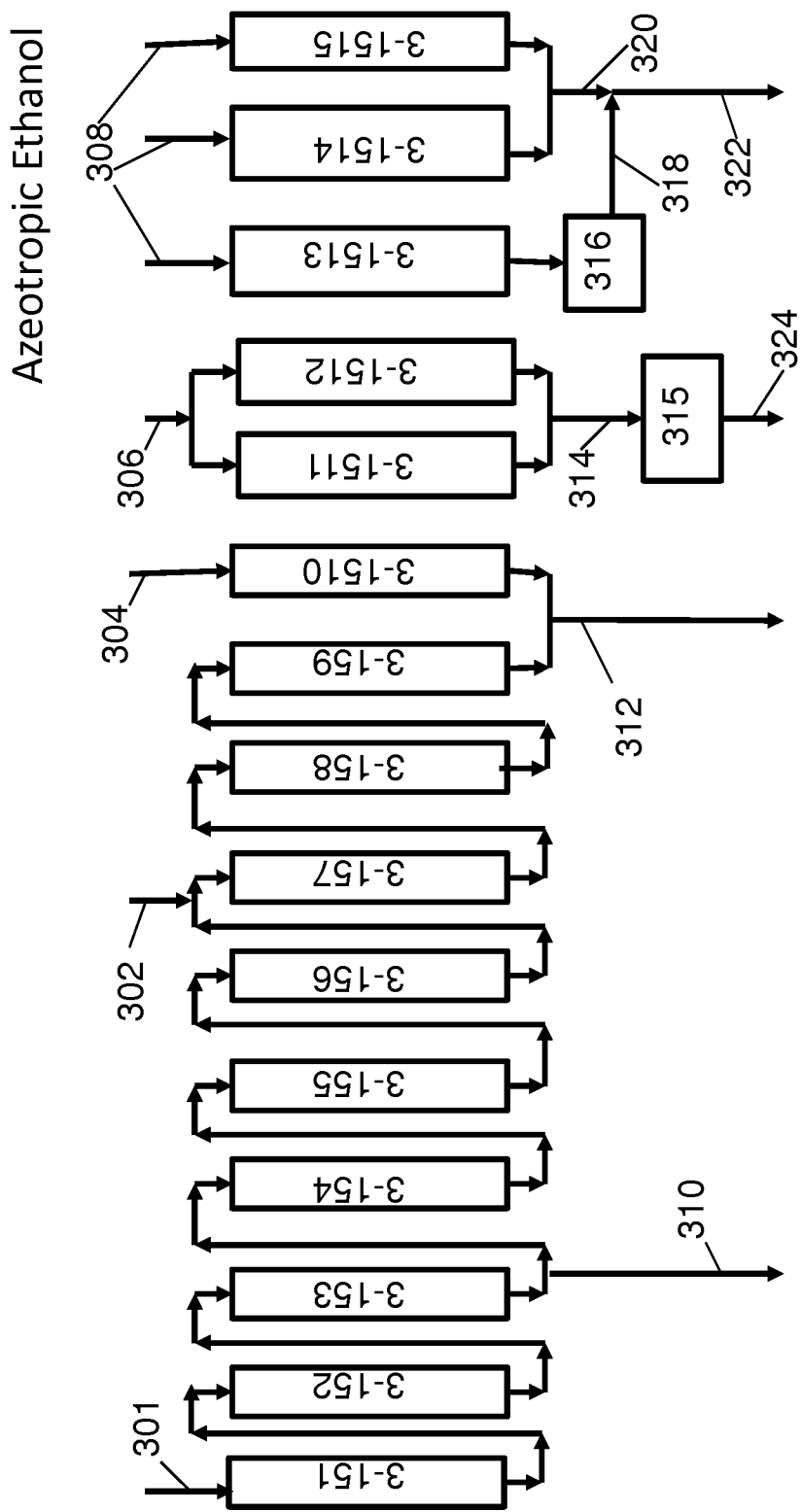
FIG. 4 is a schematic process flow diagram representing an embodiment of the present invention for a 15 adsorbent bed simulated moving bed adsorption process employing an azeotropic ethanol/water mixture as a desorbent for the dewatering of a fermentation effluent comprising ethanol and butanediol.

Referring to FIG. 4, which represents a azeotropic ethanol regeneration SMB using an azeotropic ethanol desorbent scheme for the separation of ethanol and butanediol from a fermentation effluent, a 15 adsorbent bed SMB arrangement is shown, wherein there are 15 (n=15) adsorbent beds numbered 3-151 to 3-1515 which contain a stationary phase agent as described hereinabove. The first 10 beds of the 15 adsorbent beds operate in the liquid phase and represent a desorption zone (3-151 to 3-153), a rectification zone (3-154 to 3-156), and an adsorption zone (3-157 to 3-1510). The last five adsorbent beds comprise a primary regeneration zone (3-1511 to 3-1512) and a secondary regeneration zone (3-1513 to 3-1515). Each of the adsorbent beds has a top and a bottom and a plurality of flow lines are aligned to conduct the flow of fluid from the bottom of the first adsorbent bed 3-151 in a serial manner from the bottom of adsorbent bed i to the top of adsorbent bed i+1 for adsorbent beds 3-151 to adsorbent bed 3-159. In each increment of the SMB cycle a feed stream is introduced in the top of adsorbent bed 3-157 via line 302, the mobile phase desorbent stream comprising an azeotropic mixture of ethanol and water (96/4 v:v) is introduced to adsorbent bed 3-151 via line 301, an extract stream is withdrawn from adsorbent bed 3-153 in line 310, and a primary raffinate stream comprising pure water is withdrawn from adsorbent beds 3-159 and 3-1510 via line 312 as the primary raffinate stream. A portion of the primary raffinate stream in line 312 is chilled in a chiller zone (not shown) to provide a chilled primary raffinate stream and the chilled primary raffinate stream is passed to the top of adsorbent bed 3-1510 and introduced via line 304 to purge and at least partially cool adsorbent bed 3-1510, or purge zone. A steam stream in header 306 is passed to the top of adsorbent beds 3-1511 and 3-1512 (a first hot regeneration zone) to purge ethanol from adsorbent bed 3-1511 and 3-1512 to provide a hot ethanol stream or first hot regeneration effluent stream in manifold 314. Adsorbent beds 3-1513 to 3-1515 arranged in parallel to form a second hot regeneration zone and are purged with a heated azeotropic ethanol stream having a regeneration temperature of from about 110° C. to about 130° C. and introduced at the top of the adsorbent beds 3-1512 to 3-1515 via manifold 308 and the second hot regeneration zone effluent is collected in manifold 320. Because adsorbent bed 3-1513 is at a higher temperature than adsorbent bed 3-1515, all or a portion of the effluent from adsorbent bed 3-1513 is condensed in condenser 316 and collected in line 318. The effluent in lines 318 and 320 is combined to provide an azeotropic ethanol stream or second secondary raffinate stream in line 322. All or a portion of the azeotropic ethanol stream in line 322 can be recycled directly to be combined or to supply a portion of the mobile phase desorbent stream in line 301 or to provide a portion of the superheated ethanol stream in line 308. The hot ethanol stream comprising water and ethanol in manifold 314 is condensed to provide a condensed ethanol recycle stream, or first secondary raffinate stream in line 324 and passed to the extract column (not shown) for further separation of ethanol.

Figure 5:
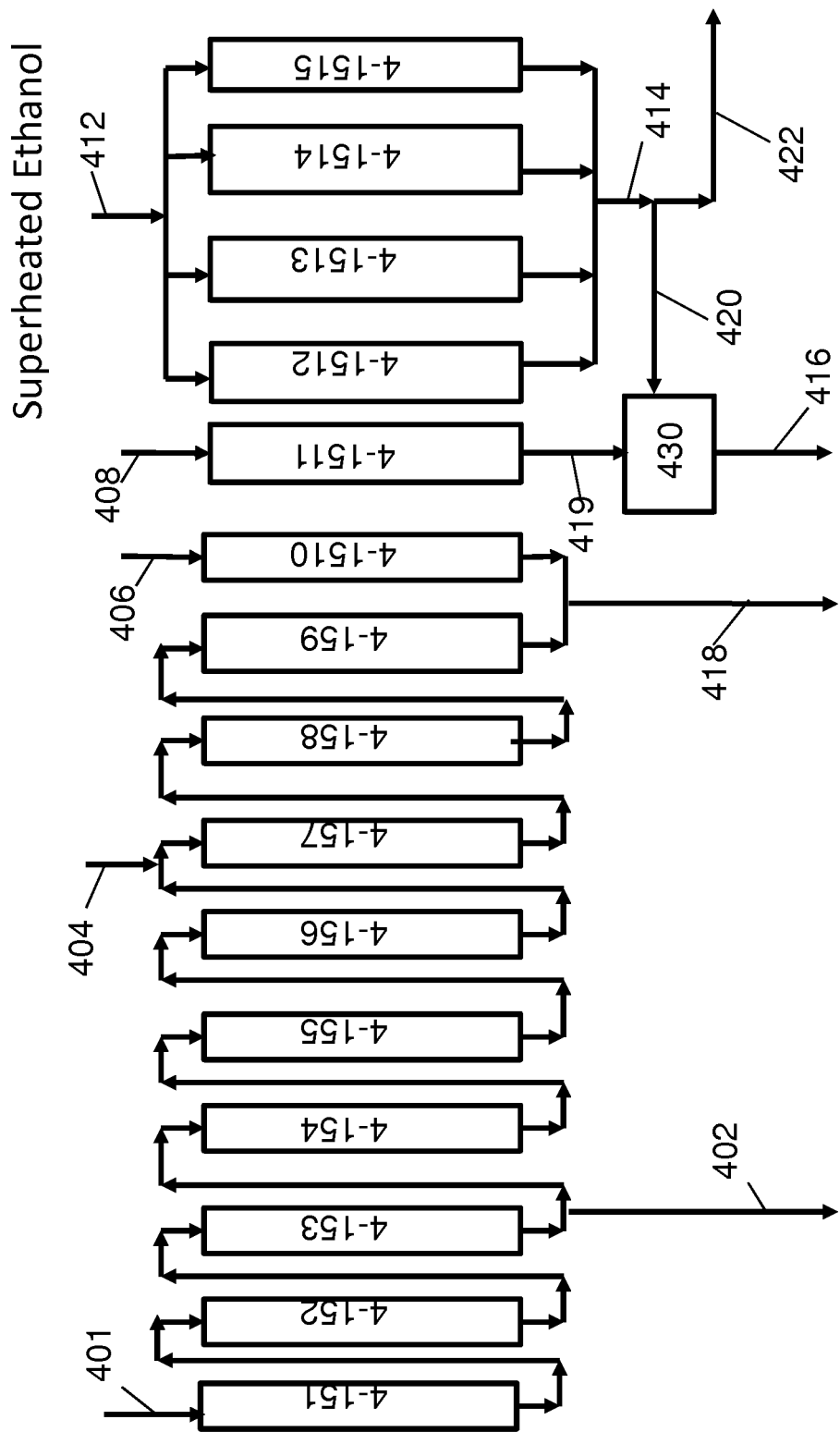
FIG. 5 is a schematic process flow diagram representing an embodiment of the present invention for a 15 adsorbent bed simulated moving bed adsorption process employing a ethanol vapor stream as a desorbent for the dewatering of a fermentation effluent comprising ethanol and butanediol.

Referring to FIG. 5, which represents a superheated ethanol regeneration SMB scheme using a superheated ethanol mobile phase desorbent for the separation of ethanol and butanediol from a fermentation effluent, a 15 adsorbent bed SMB arrangement is shown, wherein there are 15 adsorbent beds numbered 4-151 to 4-1515 which contain a stationary phase agent as described hereinabove. The first 9 beds of the 15 adsorbent beds operate in the liquid phase and represent a desorption zone (4-151 to 4-153), a rectification zone (4-154 to 4-156), and an adsorption zone (4-157 to 4-159). The last six adsorbent beds comprise a liquid regeneration zone (4-1510) a primary regeneration zone or purge zone (4-1511) and a secondary regeneration zone or hot regeneration zone (4-1512 to 4-1515). Each of the adsorbent beds has a top and a bottom and a plurality of flow lines are aligned to conduct the flow of fluid from the bottom of the first adsorbent bed 4-151 in a serial manner from the bottom of adsorbent bed i to the top of adsorbent bed i+1 for adsorbent beds 4-151 to adsorbent bed 4-159. In each increment of the SMB cycle a feed stream is introduced in the top of adsorbent bed 4-157 via line 404, the mobile phase desorbent stream comprising pure ethanol is introduced to adsorbent bed 4-151 via line 401, an extract stream is withdrawn from adsorbent bed 4-153 in line 402, and a raffinate stream is withdrawn from adsorbent beds 4-159 and 4-1510 via line 418. A portion of the raffinate stream in line 418 is passed to the top of adsorbent 4-1510 via line 408 to purge and cool adsorbent bed 4-1510. A nitrogen stream in line 408 is passed to the top of adsorbent bed 4-1511 to purge ethanol from adsorbent bed 4-1511 to provide a hot ethanol stream in line 419. Adsorbent beds 4-1512 to 4-1515 arranged in parallel and are purged with a superheated ethanol stream introduced at the top of the adsorbent beds 4-1512 to 4-1515 via manifold 412 and the effluent is collected in manifold 414 and passed in line 420 together with the contents of line 419 to a condenser 430 to condense the pure ethanol and provide a condensed ethanol stream in line 416. At least a portion of the pure ethanol stream can be returned to the SMB to provide a portion of the mobile phase desorbent stream in line 201.

Figure 6:
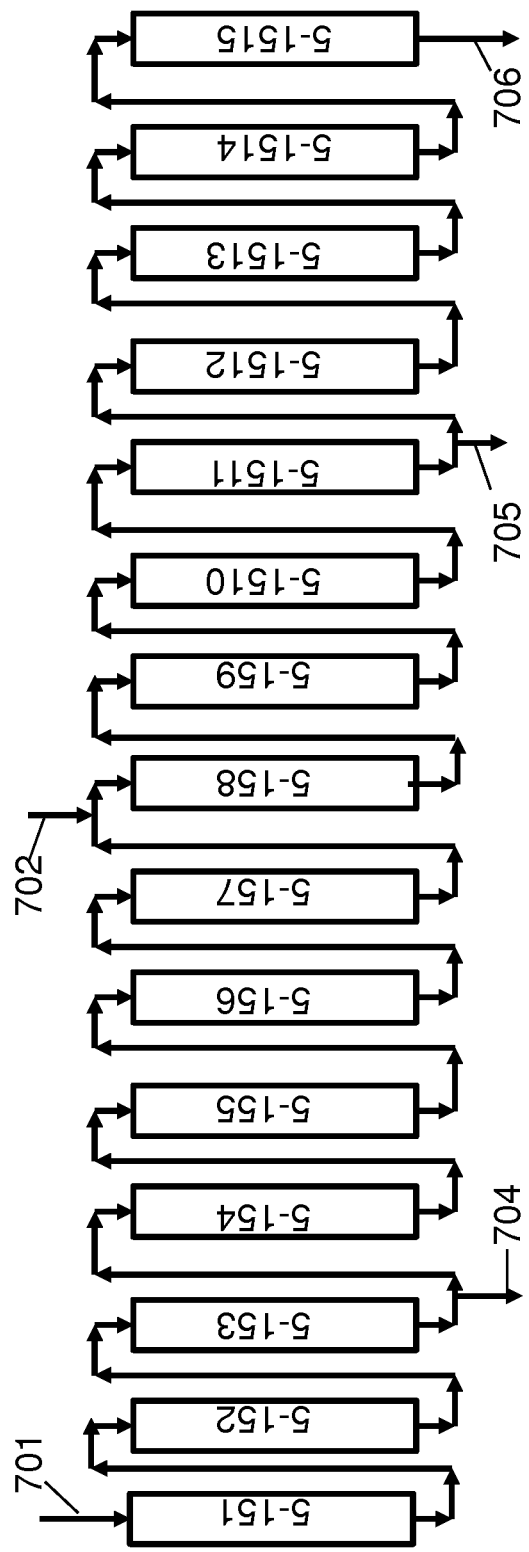
FIG. 6 is a schematic process flow diagram representing an embodiment of the present invention for a 15 adsorbent bed simulated moving bed adsorption process employing a methanol stream as a desorbent for the dewatering of a fermentation effluent comprising ethanol and butanediol with two raffinate streams.

Referring to FIG. 6, which represents an all liquid phase embodiment of the present invention, an SMB using a methanol desorbent scheme for the separation of ethanol and butanediol from a fermentation effluent which produces an extract and 2 raffinate streams (a primary raffinate and a secondary raffinate stream). In FIG. 6, a 15 adsorbent bed SMB arrangement is shown, wherein there are 15 adsorbent beds numbered 5-151 to 5-1515 which contain a stationary phase agent as described hereinabove. All 15 adsorbent beds operate in the liquid phase and represent a desorption zone (5-151 to 5-153), a rectification zone (5-154 to 5-157), and an adsorption zone (5-157 to 5-1511). The last four adsorbent beds comprise a liquid regeneration zone (5-1512-5-1515). Each of the adsorbent beds has a top and a bottom and a plurality of flow lines are aligned to conduct the flow of fluid from the bottom of the first adsorbent bed 5-151 in a serial manner from the bottom of adsorbent bed i to the top of adsorbent bed i+1 for adsorbent beds 5-151 to adsorbent bed 5-1515. In each increment of the SMB cycle a feed stream is introduced in the top of adsorbent bed 5-158 via line 702, the mobile phase desorbent stream comprising pure methanol is introduced to adsorbent bed 5-151 via line 701, an extract stream is withdrawn from adsorbent bed 5-153 in line 704, and a primary raffinate stream comprising 100% water is withdrawn from adsorbent bed 5-1511 via line 705, and a secondary raffinate stream comprising methanol and water is withdrawn from adsorbent bed 5-1515 in line 706. At least a portion of the secondary raffinate stream in line 706 is passed to a methanol distillation zone (not shown) to remove water and recover a pure methanol stream which can be returned or recycled to the SMB zone to provide at least a portion of the mobile phase desorbent stream in line 701.

Figure 7:
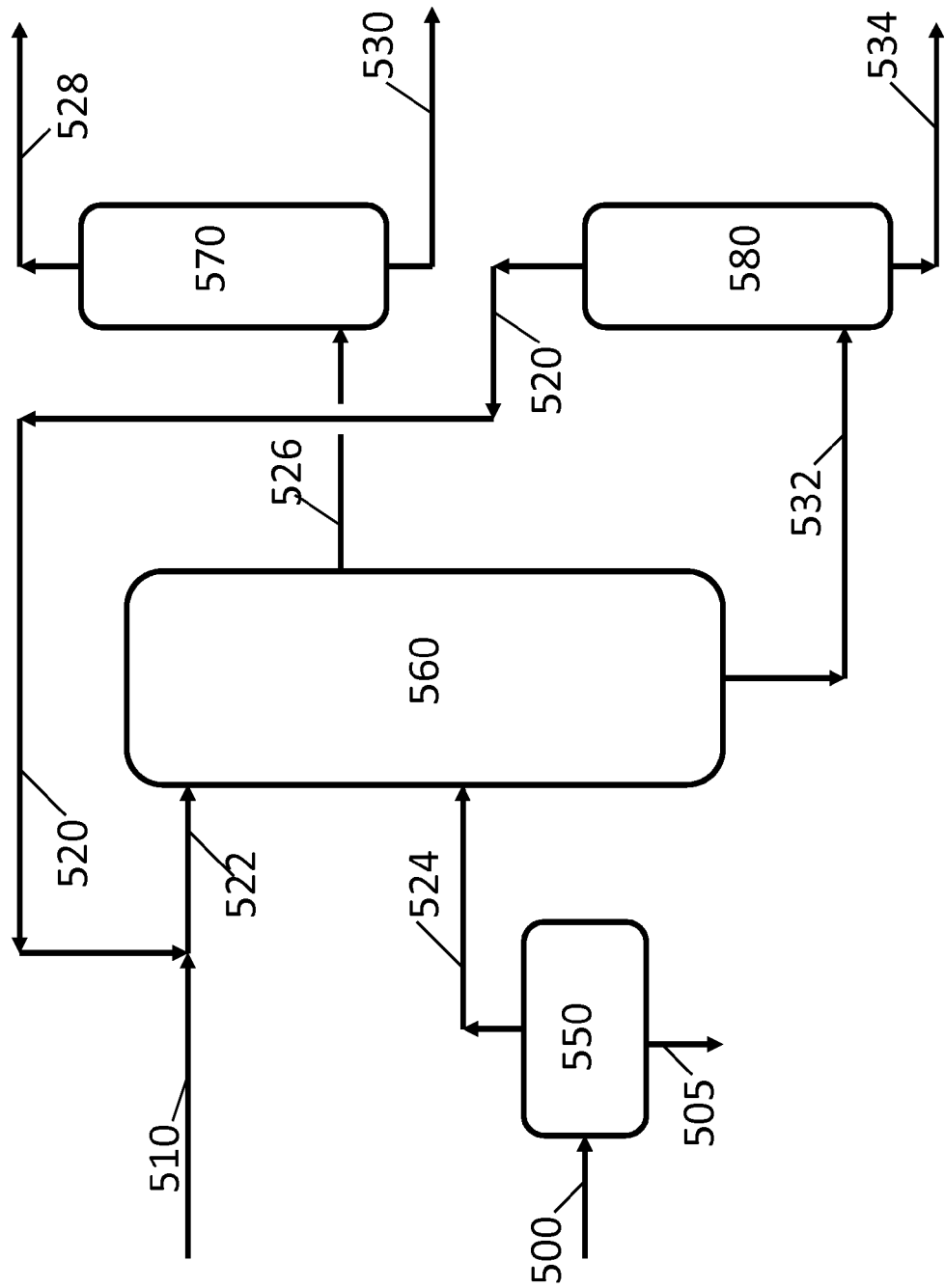
FIG. 7 is a schematic process flow diagram representing an embodiment of the present invention for a simulated moving bed adsorption process illustrating the separate recovery of ethanol product, and 2,3-butanediol employing an external ethanol distillation column.

Referring to FIG. 7 show integration SMB scheme with azeotropic ethanol/pure desorbents. Referring to FIG. 7, a fermentation broth in line 500 is passed to a pretreatment zone 550 to provide a treated feed stream in line 524 and a residue biomass stream in line 505 which is returned to the fermentation zone (not shown). The treated feed stream in line 524 and a mobile phase desorbent stream in lines 510 and 522 is passed to an SMB zone 560. The SMB zone 560 is operated as described hereinabove in FIG. 3 or FIG. 4. An extract stream is withdrawn from the SMB zone 560 in line 526, and a raffinate stream comprising water and desorbent is withdrawn from the SMB zone 560 in line 532. The raffinate stream in line 532 is passed to a raffinate separation zone 580, such as a distillation zone, to remove water in a raffinate separation zone bottoms stream in line 534, and to provide a desorbent recycle stream in line 520, wherein all or at least a portion of the desorbent recycle stream in line 520 can be returned to be admixed with the desorbent stream in lines 522. The extract stream in line 526 comprising ethanol, butanediol and desorbent is passed to an extract/desorbent separation zone 570 comprising a distillation column to provide an overhead stream comprising the desorbent in line 528 and a bottoms stream in line 530 comprising ethanol and butanediol. When the desorbent is ethanol, such as azeotropic ethanol, a portion of the overhead stream in line 528 may be recovered as an azeotropic mixture of ethanol and water and either a portioned returned to the SMB zone for use as the mobile phase desorbent (not shown) or recovered as an azeotropic mixture or further purified to provide a pure ethanol product (not shown). The bottoms stream in line 530 from the extract/desorbent separation zone 560 is passed to a product recovery zone (not shown) for the recovery of the ethanol and butanediol products. In the context of the scheme illustrated by FIG. 6, multiple distillation columns 570 and 580 are required to purify the raffinate stream or remove components to provide an overhead stream which can be returned to the SMB zone 560 as the mobile phase desorbent stream in line 522. This additional distillation step as significantly to the capital cost and to the daily operating cost of the process. In the scheme which employs azeotropic ethanol mobile phase desorbent as shown in FIG. 4, less energy is required compared to the methanol desorbent scheme. However in the azeotropic ethanol scheme there is a requirement for a high flow rate of recycled refrigerant to condense the steam and the residual ethanol recovered in the regeneration steps. This high flow rate increases the overall size of the entire SMB zone.

FIG. 8 shows the integration of the SMB zone in a process scheme with superheated ethanol regeneration as described hereinabove in FIG. 5. FIG. 8 represents a further embodiment which results in significant utility and capital cost savings over both the methanol and the azeotropic mobile phase desorbent schemes described hereinabove. These capital and operating costs are realized by the elimination of the separate raffinate distillation zone. Referring to FIG. 8, fermentation broth in line 600 is passed to a pretreatment zone 650 to provide a treated feed stream in line 624 and a residue biomass stream in line 605 which is returned to the fermentation zone (not shown). The treated feed stream in line 624 and a mobile phase desorbent stream in lines 610 and 622 is passed to an SMB zone 660. The SMB zone 660 is operated as described hereinabove in FIG. 5. An extract stream is withdrawn from the SMB zone 660 in line 626, and a raffinate stream comprising water and desorbent is withdrawn from the SMB zone 560 in line 632. All or at least a portion of the raffinate stream in line 632 (comprising the primary raffinate stream 418 as shown in FIG. 5) is recycled directly to the SMB zone 660 via lines 632, 620 and 622. The condensed ethanol stream 628 (Sown in FIG. 5 as line 416) is combined with the extract stream 626 and passed to an ethanol separation zone 670 comprising a distillation column. The ethanol separation zone 670 provides an overhead ethanol stream which can be returned to the SMB zone as the mobile phase desorbent in lines 634 and 620 and 622, or withdrawn as an intermediate ethanol product stream in line 640. An ethanol column bottoms stream comprising ethanol and butanediol is withdrawn from the ethanol separation zone 670 in line 630 and passed to a product recovery zone (not shown) to recover butanediol and ethanol.

In all of the embodiments or schemes described hereinabove, the extract stream contains <0.5 wt-% water.

In a commercial implementation of the present invention, the number of actual adsorbent beds in zone of the SMB is a matter of economic choice and valve size limitations. For example, in an all liquid SMB process which uses methanol as the mobile phase desorbent and produces three raffinate streams, the eight bed SMB unit will comprise 2 adsorbent beds in the desorption zone, 3 adsorption beds in the rectification zone, 1 adsorbent bed in the adsorption zone, 1 bed in the primary regeneration zone and one adsorbent bed in the secondary regeneration zone, or an SMB configuration 2-3-

1-1-1. In a similar 15 SMB for the same process, the SMB will have an SMB configuration 3-4-4-2-2.

The present invention is further described and illustrated by the following material balance and economic comparison based on engineering calculation and laboratory data for plant performance.

Material Balance Comparison

Material balances were prepared for the ethanol and butanediol SMB schemes according to the number of raffinate products provided by the various schemes and the mobile phase desorbent and regeneration zone operation. The following schemes were compared. The overall material balances for the above cases are shown in Table 1.

| Case | Reference FIG. | SMB Scheme |
|---|---|---|
| A | FIG. 3 or FIG. 4 | Ethanol desorption with steam regeneration |
| B | FIG. 5 | Ethanol desorption, N2 displacement, superheated ethanol vapor regeneration |
| C | FIG. 2 | Methanol desorption scheme with 3 raffinate streams |
| D | FIG. 6 | Methanol desorption scheme with 2 raffinate streams |
| E | FIG. 1 | Methanol desorption scheme with 1 raffinate stream |

D, there were 2 raffinate streams; and in Case E, there was a single raffinate stream as disclosed in the parent case, U.S. application Ser. No. 13/478,160. In all of the methanol desorbent cases, at least one raffinate stream comprised from about 25 to about 50 wt-% methanol in water which required the recovery of methanol by distillation to provide a recycle pure methanol desorbent stream which was admixed with the mobile phase desorbent stream passed to the SMB zone. By way of example and with reference to FIG. 6, a two raffinate scheme, the primary raffinate stream in line 705, comprises water and the secondary raffinate stream comprises about 50 wt-% methanol in water. This scheme requires about 57 percent of the distillation load as Case E, wherein there is a single raffinate stream comprising about 28.5 wt-% methanol. In case C, with three raffinate streams, the primary raffinate stream comprises water, the secondary raffinate stream comprises about 26 wt-% methanol in water, and the tertiary raffinate stream comprises 100 wt-% methanol. A distillation zone is still required to recovery methanol, but the capacity of the distillation zone in Case C is less than 55 percent of the distillation capacity required in Case E of the parent case.

Economic Comparison

An economic analysis was developed based on actual SMB plant data and engineering cost estimates for the hereinabove describes SMB operations employing methanol as the mobile phase desorbent (Cases C-E), and azeotropic ethanol as the mobile phase desorbent (Cases A and B). The economic

TABLE 1

MATERIAL BALANCE SUMMARY COMPARISON

| SMB Scheme | Extract | | Primary Raffinate | | Secondary Raffinate-I | | Secondary Raffinate-II | |
|---|---|---|---|---|---|---|---|---|
| | Flow Rate (MMKg/Day) | Composition | Flow Rate (MMKg/Day) | Composition | Flow Rate (MMKg/Day) | Composition | Flow Rate (MMKg/Day) | Composition |
| A Ethanol desorption with steam regeneration* | 1.230 | Water: 1% Ethanol: 34% BDO: 7% | 8.686 | 0.2% EtOH in water | NA | NA | NA | NA |
| B Ethanol desorption, N2 displacement, superheated ethanol vapor regeneration | 1.230 | Water: 1% Ethanol: 34% BDO: 7% | 5.517 | 0.2% EtOH in water | NA | NA | NA | NA |
| C Methanol desorption scheme with 3 raffinate streams | 0.871 | Water: 1% Ethanol: 34% BDO: 7% Methanol: 58% | 3.685 | 100% Water | 3.273 | 26% MeOH in water | 1.588 | 100% Methanol |
| D Methanol desorption scheme with 2 raffinate stream | 0.871 | Water: 1% Ethanol: 34% BDO: 7% Methanol: 58% | 3.685 | 100% Water | 4.861 | 50.2% Methanol in Water | NA | NA |
| E Methanol desorption scheme with 1 raffinate stream | 0.871 | Water: 1% Ethanol: 34% BDO: 7% Methanol: 58% | 8.547 | 28.5% Methanol in water | NA | NA | NA | NA |

Material Balance Comparison

With reference to Table 1, a material balance is shown for the hereinabove described 5 different SMB purification and recovery schemes based on the production of the same amount of ethanol in the extract stream. In cases A and B, the desorbent mobile phase is azeotropic ethanol having about 0.2 wt-% ethanol in water, and a portion of the raffinate stream is returned to the SMB zone to provide a portion of the mobile phase desorbent stream passed to the SMB zone, or employed to regenerate a portion of the SMB zone (See FIG. 4). Cases C, D, and E represent the use of methanol as the mobile phase desorbent with SMB configurations which differ by the number of raffinate streams withdrawn from the SMB zone. In Case C, there were 3 raffinate streams; in Case analysis was based on a fermentation broth comprising ethanol and 2,3 butanediol for an SMB plant producing 120,000 MTA (metric tonnes per annum) of total alcohol. Table 2 shows a comparison of the capital and operating costs for Cases A-E. The results of this analysis clearly show that for the use of a methanol mobile phase desorbent, employing an SMB scheme having more than a single raffinate stream significantly reduces the operating costs associated with recovering the methanol. With a methanol mobile phase desorbent, Case C achieves a significant savings in daily operating costs over both Case D and Case E. As shown in Table 2, the Total Operating cost per annum for the methanol Case D, having two raffinate stream resulted in a 34 percent reduction compared to Case E having a single raffinate stream, and the Total Operating Cost per annum in Case C having three raffinate streams resulted in a about a 58 percent reduction compared to Case E having a single raffinate stream. When ethanol was used as the mobile phase desorbent combined with heated regeneration as described in FIGS. 3, 4, and 5, the Total Operating was also significantly lower than the single raffinate methanol desorbent schemes in Case D and E. The addition of a nitrogen displacement step to purge or remove any remaining vapor from the adsorbent bed prior to the transition to the liquid phase operation combined with vapor phase regeneration by superheated ethanol as exemplified in Case B provided significant capital cost and operating costs compared to all of the methanol desorbent cases (Cases C-E) and the steam regeneration case using ethanol desorbent in Case A. Furthermore, both Case A and Case B do not have the problem of potentially contaminating the fermentation zone by returning a biomass recycle stream contaminated with methanol.

TABLE 2

Economic Comparison of SMB Zone Regeneration Methods

| | Case A | Case B | Case C | Case D | Case E |
|---|---|---|---|---|---|
| Reference FIG. | FIG. 3 & 4 | FIG. 5 | FIG. 2 | FIG. 6 | FIG. 1 |
| Desorbent | Ethanol Steam Regen | Ethanol/$N_2$, Superhtd ethanol vapor Regen | Methanol w/3 Raffinates* | Methanol/ w/2 Raffinates | Methanol w/1 Raffinate |
| Total Desorbent, MT/D | 352 | 352 | 352 | 352 | 352 |
| Steam, MT/D | | | | | |
| Steam Cost, $/MT | | | | | |
| Distillation Heat Load, MJ/MT total alcohol | 52104 | 9029 | 16738 | 25804 | 39752 |
| Total Operating Cost per Annum, $MM | 31 | 17 | 24 | 37 | 57 |
| SMB Cap. Cost, MM$ | 15 | 32 | 32 | 32 | 32 |
| Dist. Column Cost, MM$ | 3 | 5 | 19 | 19 | 19 |
| Total Capital Cost, $MM | 18 | 37 | 51 | 51 | 51 |

*Case B scheme based on nitrogen purge in the primary regeneration zone and a secondary regeneration zone employing superheated ethanol regeneration.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure and the following claims.

We claim:

1. A multi-raffinate simulated moving bed (SMB) process for the separation of ethanol and butanediol from an aqueous biomass effluent stream from a fermentor, said biomass effluent stream comprising water, ethanol, butanediol, acetic acid, and suspended solids, said multi-raffinate SMB process having an SMB zone comprising a desorption zone, a rectification zone, an adsorption zone, and at least one regeneration zone, said process comprising:
   a. passing the aqueous biomass effluent stream to a pretreatment zone including a naturation zone and a filtration zone to provide an SMB feed stream;
   b. passing the SMB feed stream at an effective feed temperature and a mobile phase desorbent stream at an effective desorbent temperature, said mobile phase desorbent stream comprising a $C_1$ to $C_3$ alcohol to the SMB zone comprising a plurality of n adsorbent beds each adsorbent bed having a top and a bottom, wherein the desorption zone, rectification zone, adsorption zone, and the at least one regeneration zone comprise one or more of the adsorbent beds containing a stationary phase adsorbent selected from the group consisting of a fluorinated carbon adsorbent and a modified C18 silica gel, and wherein each of the adsorbent beds of the desorption zone, rectification zone, adsorption zone are disposed in a serial configuration wherein the bottom of each adsorbent bed is in fluid communication with the top of the i+1 adsorbent bed, to provide an extract stream comprising ethanol and butanediol withdrawn from the desorption zone and a primary raffinate stream withdrawn from the adsorption zone,
   c. passing at least a portion of the primary raffinate stream to the at least one regeneration zone to provide at least one secondary raffinate stream; and,
   d. passing the extract stream to a product recovery zone to separate and recover ethanol and butanediol products from the extract stream.

2. The process of claim 1, wherein the at least one regeneration zone comprises a first liquid regeneration zone and a second liquid regeneration zone wherein at least a portion of the primary raffinate stream is passed to the first liquid regeneration zone to provide a first secondary raffinate stream, and at least a portion of the first secondary raffinate stream is passed to the second liquid regeneration zone to provide a second secondary raffinate stream.

3. The process of claim 2, wherein the mobile phase desorbent is pure methanol and the primary raffinate stream consists essentially of water, the first secondary raffinate comprises a mixture of methanol and water, and the second secondary raffinate stream consists essentially of methanol.

4. The process of claim 3, wherein the primary raffinate stream comprises from about 98 to about 99.99 vol-% water.

5. The process of claim 3, wherein the second secondary raffinate stream comprises from about 99.0 to about 99.999 vol-% methanol.

6. The process of claim 3, further comprising passing the first secondary raffinate stream to a methanol distillation zone to recover a pure methanol product and returning at least a portion of the pure methanol product to provide the mobile phase desorbent stream.

7. The process of claim 1, wherein the mobile phase desorbent comprises ethanol and the at least one regeneration zone comprises a liquid regeneration zone, a purge zone, and a hot regeneration zone, said process further comprising:
   a. cooling the portion of the primary raffinate stream to a chilled raffinate temperature to provide a cooled primary raffinate portion and passing the cooled primary raffinate portion to the liquid regeneration zone to provide an intermediate raffinate stream and admixing the intermediate raffinate stream with the primary raffinate stream to provide a combined primary raffinate stream,
   b. passing an inert gas selected from the group consisting of nitrogen or carbon dioxide to the purge zone to provide a purge zone effluent stream and condensing the purge zone effluent stream to provide a first secondary raffinate stream;
   c. passing a hot regeneration stream comprising hot water or steam or azeotropic ethanol to the hot regeneration zone to provide a hot regeneration effluent stream, and,
   d. condensing all or at least a portion of the hot regeneration effluent stream to provide a condensed regeneration effluent stream, and,
   e. withdrawing the condensed regeneration effluent stream as a second secondary raffinate stream or admixing the condensed regeneration effluent stream with the first secondary raffinate stream to provide a combined secondary raffinate stream.

8. The process of claim 7, wherein the mobile phase desorbent comprises an azeotropic mixture of ethanol and water and at least a portion of the second secondary raffinate stream comprising the azeotropic mixture of ethanol and water is returned to step (c) as the hot regeneration stream.

9. The process of claim 7, wherein the hot regeneration stream comprises a superheated ethanol stream comprising substantially pure ethanol.

10. The process of claim 9, wherein the superheated ethanol stream has a superheated temperature of from about 110° C. to about 130° C.

11. The process of claim 7, wherein the portion of the primary raffinate stream cooled in step (c) is cooled to a chilled raffinate temperature ranging from about 20° C. to about 50° C.

12. The process of claim 7, wherein the effective desorbent temperature ranges from about 50° C. to about 80° C.

13. The process of claim 7, wherein the at an effective feed temperature ranges from about 20° C. to about 50° C.

14. The process of claim 9, further comprising passing the first secondary raffinate stream to a distillation zone for the recovery of an ethanol product.

15. The process of claim 2, wherein the number of adsorbent beds is 15 having an SMB configuration of 3-4-4-2-2.

16. The process of claim 2, wherein the number of adsorbent beds is 8 having an SMB configuration of 2-3-1-1-1.

* * * * *